US008362090B2

(12) United States Patent
Oben

(10) Patent No.: US 8,362,090 B2
(45) Date of Patent: *Jan. 29, 2013

(54) METHODS AND RELATED COMPOSITIONS USING SPECIFIC FLAVONOIDS AND INDANES TO REDUCE WEIGHT AND INHIBIT LIPASE, α-AMYLASE AND α-GLUCOSIDASE ACTIVITY IN MAMMALS

(75) Inventor: Julius Enyong Oben, Yaounde (CM)

(73) Assignee: Gateway Health Alliances, Inc., Fairfield, CA (US)

( * ) Notice: Subject to any disclaimer, the term of this patent is extended or adjusted under 35 U.S.C. 154(b) by 461 days.

This patent is subject to a terminal disclaimer.

(21) Appl. No.: 12/685,990

(22) Filed: Jan. 12, 2010

(65) Prior Publication Data

US 2010/0113374 A1    May 6, 2010

Related U.S. Application Data

(63) Continuation of application No. 11/855,084, filed on Sep. 13, 2007, now Pat. No. 7,659,313.

(51) Int. Cl.
*A01N 31/00* (2006.01)
*A01N 59/00* (2006.01)
*A61K 31/045* (2006.01)
*A61K 33/00* (2006.01)
*C09B 31/00* (2006.01)
*C09B 33/00* (2006.01)
*C09B 35/00* (2006.01)
*C09B 37/00* (2006.01)

(52) U.S. Cl. ......... 514/909; 514/724; 424/725; 534/659
(58) Field of Classification Search .................. 514/909, 514/724; 424/725; 534/659
See application file for complete search history.

(56) References Cited

U.S. PATENT DOCUMENTS

| 3,368,903 | A | 2/1968 | Johnson et al. |
| 5,736,532 | A | 4/1998 | Furda |
| 6,583,118 | B1 | 6/2003 | Watanabe et al. |

FOREIGN PATENT DOCUMENTS

| EP | 785214 A2 | 7/1997 |
| JP | 10182469 A | 7/1998 |
| JP | 11050050 A | 2/1999 |
| JP | 2006-8523 | * 1/2006 |
| WO | WO 03/020677 A2 | 3/2003 |
| WO | WO 03/105766 A2 | 12/2003 |

OTHER PUBLICATIONS

Machine translation of JP 2006-008523 (2006) [online] [Retrieved May 11, 2012] Retrieved from the internet <http://dossier1.ipdl.inpit.go.jp/AIPN/odse_top_dn.ipdl?N0000=7400>.*
Ritu Trivedi, Sudhir Kumar, Avinash Kumar, Jawed A. Siddiqui, Gaurav Swarnkar, Varsha Gupta, Amruta Kendurker, Anil Kumar Dwivedi, Jose R. Romero, Naibedya Chattopadhyay; Kaempferol has osteogenic effect in ovariectomized adult Sprague-Dawley rats; Molecular and Cellular Endocrinology; 2008; 85-93; vol. 289; Elsevier.
Hazel Sharp, Jackie Hollinshead, Barbara Bartholomew, Julius Oben, Alison Watson, Robert Nash; Inhibitory Effects of *Cissus quadrangularis* L. Derived Components on Lipase, Amylase and Glucosidase Activity in vitro; Natural Product Communications; 2007; 817-822; vol. 2, No. 8.
Julius Oben, Dieudonne Kuate, Gabriel Agbor, Claudia Momo, Xavio Talla; The Use of *Cissus quadrangularis* formulation in the management of weight loss and metabolic syndrome; Lipid World; Sep. 2, 2006; vol. 5, No. 24; BioMed Central.
Kiyofumi Ninomiya, Hisashi Matsuda, Mizuho Kubo, Toshio Morikawa, Norihisa Nishida, Masayuki Yoshikawa; Potent anti-obese principle from Rosa canina: Structural requirement and mode of action of trans-tiliroside; Bioorganic & Medicinal Chemistry Letters; Mar. 18, 2007; 3059-3064; vol. 17; Elsevier.
Jainu, Mallika, et al. "Gastroprotective effect of *Cissus quadrangularis* extract in rats with experimentally induced ulcer." *Indian J Med* Res 123, Jun. 2006, pp. 799-806, Department of Biochemistry, University of Madras, Chennai, India.
Jainu, M., et al. "Gastroprotective action of *Cissus quadrangularis* extract against NSAID induced gastric ulcer: role of proinflammatory cytokines and oxidative damage." *Chemico-Biological Interactions*, Jul. 10, 2006;161(3):262-70. Epub May 1, 2006.
Jo, Moody, et al. "Anti-sickling potential of a Nigerian herbal formula (ajawaron HF) and the major plant component (*Cissus populnea* L. CPK)." *Phytother Res.*, Dec. 2003; 17(10):1173-6.
Phondke, G.P., ed. *The Wealth of India: A Dictionary of Indian Raw Materials & Industrial Products*. "Raw Materials, vol. 3: Ca-Ci (Revised)." 1992, pp. 593-594. Publications & Information Directorate, Council of Scientific & Industrial Research, New Delhi.
Sen, S.P. "Study of the Active Constituents (Ketosteroids) of *Cissus quadrangularis*, Wall." *The Indian Journal of Pharmacy*, Sep. 1964, p. 247.
Mehta, Manisha. "Determination of Marker Constituents from *Cissus quadrangularis* Linn. and their Quantitation by HPTLC and HPTLC." *Phytochemical Analysis*, 2001:12, pp. 91-95. John Wiley & Sons, Ltd.
Subbu, V.S. Venkata. "Pharmacological and Toxicological Evaluation of an Active Principle Obtained from the Plant *Vitis quadrangularis*." *Ind.J. Pharmac.* (1970), 2 (3), pp. 91-97.
Prasad, G.C., et al. "Pathways and Site of Action of a Phytogenic Steroid from *Cissus quadrangularis*." *Jour. Res. Med.* (1972), 7:4, pp. 29-35.
Singh, S.P., et al. "An Experimental Study of Analgesic Activity of *Cissus quadrangularis*." *Indian Journal of Pharmacology*, pp. 162-163, (1984).

(Continued)

Primary Examiner — Scarlett Goon
(74) Attorney, Agent, or Firm — Steve P. Hassid; Silicon Edge Law Group, LLP

(57) ABSTRACT

The present invention relates generally to methods and related compositions using flavonoids and/or indanes extracted from the stems and leaves of *C. quadrangularis* to reduce weight and inhibit lipase, α-amylase and α-glucosidase activity in mammals. By example and not by way of limitation, embodiments of the present disclosure, a composition and related methods for reducing body weight and/or inhibiting any combination of lipase, α-amylase and α-glucosidase is provided. The composition contains an effective amount of one or more flavonoids or indanes selected from 3-O-rhamnopyranosylkaempferol, 3-(4-hydroxybenzylidene)-2-(2,5-dihydroxyphenyl)-1-(4-hydroxyphenyl)indane-4,6-diol, quercitrin, rhamnitrin, rhamnocitrin, quercitrin-3-O"-acetate and parthenocissin A.

2 Claims, 1 Drawing Sheet

OTHER PUBLICATIONS

Prasad, G.C., et al. "Effect of *Cissus quadrangularis* on the Healing of Cortisone Treated Fractures." *Indian Journal of Medicine*, Jul. 1963, 51(4), pp. 667-676.

Udupa, K.N., et al. "The Effect of Phytogenic Anabolic Steroids in the Acceleration of Fracture Repair." *Life Sciences*, 1965, vol. 4, pp. 317-327. Pergamon Press, Ltd., Great Britain.

Chopra, S.S., et al. "Studies on *Cissus quadrangularis* in Experimental Fracture Repair: A Histopathological Study." *Indian J. Med. Res.*, Sep. 1976, 64:9, pp. 1365-1368.

Deka, D.K., et al. "Effect of *Cissus quadrangularis* in Accelerating Healing Process of Experimentally Fractured Radius-Ulna of Dog: A Preliminary Study." *Indian Journal of Pharmacology*, 1994; 26, pp. 44-45.

Obatomi, D.K, et al. "Metabolic and renal changes following the ingestion of African mistletoe extract in rats." Phytotherapy (1997); 11: 171-173.

Bell, S. et al. "An investigation of the effects of two indigenous African foods, *Detarium microcarpum* and *Cissus rotundifolia* on rat plasma cholesterol levels." Proceedings of the Nutrition Society 1993; 52(3): 372a.

Achola, K.J., et al. "Pharmacological activities of *Vernonia glabra*." International Journal of Pharmacognosy (1996); 34(2): 141-144. Abstract.

Onyechi, U.A., et al. "African plant foods rich in non-starch polysaccharides reduce postprandial blood glucose and insulin concentrations in healthy human subjects." British Journal of Nutrition (Nov. 1998); 80(5): 419-28.

Gava, A., et al. "Experimental poisoning by *Vernonia-mollisima* (Compositate) in sheep and cattle." Pesquisa Veterinaria Brasileira (1987), 7(2): 33-41.

Barakat, S.E., et al. "Effects of *Cissus quadrangularis* on goats and sheep in Sudan." Revue d'Elevage et de Medecine Veterinaire des Pays Tropicaux (1985), 38(2): 185-194.

Igile, et al., "Nutritional Assessment of *Vernonia amygdalina* Leaves in Growing Mice," J. Agric. Food Chem., 1995, 43:2162-2166.

Longanga, Otshudi et al. "In vitro antimicrobial activity of six medicinal plants traditionally used for the treatment of dysentery and diarrhoea in Democratic Republic of Congo (DRC)," Phytomedicine, 1999, 7(2):167-172.

Eriyamremu, G.E., et al. "Wholly compounded Nigerian diets alter tissue lipid profile in rats." Clinica Dietologica (1995), 22 (3-4): 101-110.

Oben, J., et al. "The use of a Cissus quadrangularis formulation in the management of weight loss and metabolic syndrome." *Lipids Health Dis.* Sep. 2, 2006; 5: 24-30.

Oben, J.E., et al. "The effect of *Cissus quadrangularis* (CQR-300) and a *Cissus* formulation (CORE) on obesity and obesity-induced oxidative stress." *Lipids Health Dis.* Feb. 4, 2007; 6: 4-12.

Ninomiya, K., et al. "Potent anti-obese principle from *Rosa canina*: structural requirements and mode of action of trans-tiliroside." *Bioorg. Med. Chem. Lett.* Jun. 1, 2007; 17(11): 3059-3064. Epub Mar. 18, 2007.

Trivedi, R., et al. "Kaempferol has osteogenic effect in ovariectomized adult Sprague-Dawley rats." *Mol. Cell Endocrinol.* Jul. 16, 2008; 289(1-2): 85-93. Epub Mar. 4, 2008.

Shirwaikar, et al., "Antiosteoporotic effect of ethanol extract of *Cissus quadrangularis* Linn. on ovariectomized rat." *Journal of Ethnopharmacology*, 89 (2-3): 245-250, 2003.

Adesanya, S. et al., "Stilbene Derivatives from *Cissus quadrangularis*." *J. Nat. Prod.*, 1999, 62 (1), 1694-1695.

Sharp, H., et al., "Inhibitory Effects of *Cissus quadrangularis* L. Derived Components on Lipase, Amylase, and α-Glucosidase Activity in vitro." *Nat. Prod. Commun.* 2/8 NPCACO 2007, p. 817-822.

* cited by examiner

FIG. 1
Tested Flavonoids and Indanes
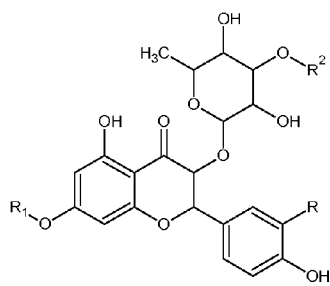
1: R = OH, R$_1$ = H, R$_2$ = H
2: R = H, R$_1$ = H, R$_2$ = H
3: R = OH, R$_1$ = CH$_3$, R$_2$ = H
4: R = H, R$_1$ = CH$_3$, R$_2$ = H
5: R = OH, R$_1$ = H, R$_2$ = COCH$_3$
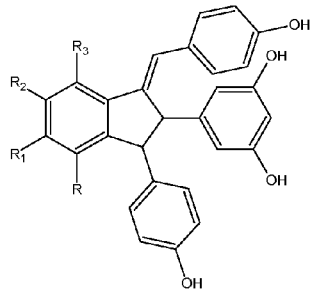
6: R = OH, R$_1$ = H, R$_2$ = OH, R$_3$ = H
7: R = H, R$_1$ = OH, R$_2$ = H, R$_3$ = OH
FIG. 2
Enzyme Inhibition Activity of Flavonoids and Indanes Showing % Inhibition
| Assay | 1 | 2 | 3 | 4 | 5 | 6 | 7 |
|---|---|---|---|---|---|---|---|
| Lipase (human pancreatic) | 51 | 55 | 47 | 52 | 60 | 41 | 35 |
| α-amylase (porcine) | 50 | 88 | 94 | 95 | 88 | 94 | 51 |
| α-glucosidase (*S. cerevisiae*) | -28 | -7 | 54 | 50 | -74 | 67 | 89 |

METHODS AND RELATED COMPOSITIONS USING SPECIFIC FLAVONOIDS AND INDANES TO REDUCE WEIGHT AND INHIBIT LIPASE, α-AMYLASE AND α-GLUCOSIDASE ACTIVITY IN MAMMALS

RELATED APPLICATION

This application is a divisional of U.S. Application Ser. No. 11/855,084, filed Sep. 13, 2007, the contents of which are incorporated by reference herein in its entirety.

BACKGROUND

*Cissus quadrangularis* L. (Vitaceae) is an ancient medicinal plant native to the hotter parts of Ceylon and India. The stems of *Cissus quadrangularis* L (Vitaceae) have been consumed for centuries throughout Asia and Africa as a culinary vegetable. *C. quadrangularis* has been used in India for promoting the fracture healing process [1] for some time. It has been prescribed in Ayurveda as an anthelmintic, dyspeptic, digestive tonic, analgesic in eye and ear diseases and in the treatment of irregular menstruation and asthma. In Cameroon, the whole plant is used in oral re-hydration, while the leaf, stem and root extracts of this plant are important in the management of various ailments. Accordingly, the safely of *C. quadrangularis*, without causing undesirable side effects, has been demonstrated over time.

There are several reports on *C. quadrangularis* use in the management of obesity and complications associated with metabolic syndrome [2], and its antioxidant and free radical scavenging activity in vitro [3,4]. Various formulations now contain extracts of *C. quadrangularis* in combination with other compounds, used for the purpose of weight management and complications/conditions resulting from these and related conditions.

Although the use of *C. quadrangularis* has been shown to provide certain benefits and advantages, it is unclear what components or aspects of *C. quadrangularis* provide what desirable benefit and advantages. Additionally, it is unclear whether certain components or aspects of *C. quadrangularis* counteract the benefits or efficacy of other components or aspects of *C. quadrangularis*. Furthermore, novel compositions and related methods which safely and effectively provide improved weight loss in a mammal, without causing undesirable side effects, is desired. Additionally, compositions and related method that safely and effectively inhibits lipase, α-amylase and α-glucosidase activity in a mammal, thereby contributing to weight loss and overall health, without causing undesirable side effects, is desired. The compositions and related methods of the present invention provide these and other related benefits and advantages.

SUMMARY OF THE INVENTION

The present invention relates to methods and related compositions using flavonoids and/or indanes extracted from the stems and leaves of *C. quadrangularis* to reduce weight and inhibit lipase, α-amylase and α-glucosidase activity in mammals. By example and not by way of limitation, in one embodiment of the present disclosure, a composition for reducing body weight or inhibiting any combination of lipase, α-amylase and α-glucosidase is provided. The composition contains an effective amount of flavonoid 3-O-rhamnopyranosylkaempferol or indane 3-(4-hydroxybenzylidene)-2-(2,5-dihydroxyphenyl)-1-(4-hydroxyphenyl)indane-4,6-diol or flavonoid 3-O-rhamnopyranosylkaempferol and indane 3-(4-hydroxybenzylidene)-2-(2,5-dihydroxyphenyl)-1-(4-hydroxyphenyl)indane-4,6-diol.

In another embodiment of the present disclosure, a method for reducing body weight in a mammal is provided. The method including providing a composition containing an effective amount of one or more flavonoids or indanes selected from 3-O-rhamnopyranosylkaempferol, 3-(4-hydroxybenzylidene)-2-(2,5-dihydroxyphenyl)-1-(4-hydroxyphenyl)indane-4,6-diol, quercitrin, rhamnitrin, rhamnocitrin, quercitrin-3-O"-acetate and parthenocissin A and claiming that the composition reduces, maintains or improves body weight in a mammal.

In yet another embodiment of the present disclosure, a method for inhibiting any combination of lipase, α-amylase and α-glucosidase in a mammal is provided. The method including providing a composition containing an effective amount of one or more flavonoids or indanes selected from 3-O-rhamnopyranosylkaempferol, 3-(4-hydroxybenzylidene)-2-(2,5-dihydroxyphenyl)-1-(4-hydroxyphenyl)indane-4,6-diol, quercitrin, rhamnitrin, rhamnocitrin, quercitrin-3-O"-acetate and parthenocissin A and claiming that the composition inhibits any combination of lipase, α-amylase and α-glucosidase in a mammal. In a detailed aspect of the present disclosure, the effective amount of the composition provided to the mammal is 10 mg to 900 mg daily. In another detailed aspect of the present disclosure, the effective amount of the composition is 50 mg to 200 mg daily.

BRIEF DESCRIPTION OF DRAWINGS

FIG. 1 demonstrates the seven flavonoid and indanes that were tested for their ability to inhibit lipase, α-amylase and α-glucosidase.

FIG. 2 is a chart summarizing the experimental results, in % inhibition, of the enzyme inhibition activity of the seven flavonoids and indanes listed in FIG. 1. Samples were tested at 0.15 mg/ml (lipase), 0.12 mg/ml (amylase) and 0.28 mg/ml (glucosidase) and the results are mean values (n=3).

DETAILED DESCRIPTION

Phytochemical analyses of *C. quadrangularis* have revealed high contents of ascorbic acid, carotene, anabolic steroidal substances and calcium. The stem contains two asymmetric tetracyclic triterpenoids, and two steroidal principles [5]. The presence of β-sitosterol, δ-amyrin and δ-amyrone has also been reported. All of these components have potentially different metabolic and physiological effects. Through experiments we performed, two novel components of *C. quadrangularis*, flavonoid (3-O-rhamnopyranosylkaempferol) and indane (3-(4-hydroxybenzylidene)-2-(2,5-dihydroxyphenyl)-1-(4-hydroxyphenyl)indane-4,6-diol), demonstrated inhibition of enzymes known to effect weight loss in mammals.

More specifically, our experiments, which are discussed in detail below, have shown that aqueous extracts of *C. quadrangularis* stems and leaves contains specific flavonoids and/or indanes which inhibit lipase, amylase and/or α-glucosidase and, therefore, are least in part related to the anti-obesity activity of the plant. The enzyme inhibition activity of a novel flavonoid (3-O-rhamnopyranosylkaempferol) and indane (3-(4-hydroxybenzylidene)-2-(2,5-dihydroxyphenyl)-1-(4-hydroxyphenyl)indane-4,6-diol) (7) and four known structurally related flavonoids and one indane isolated from the extract were tested.

Preliminary extraction and bioassays had shown that aqueous extracts of *C. quadrangularis* stems/leaves inhibited pig amylase, human lipase and yeast α-glucosidase. The inhibition of these enzymes was shown to be selective by comparison with the lack of activity against a panel of other commercially (Sigma) available enzymes including β-glucosidase (almond), α-(green coffee beans) and β-galactosidase (*A. niger*) and α-fucosidase (human). Bioassay guided fractionation of the extract was performed using the assays for amylase, lipase and α-glucosidase. The aqueous plant extract was passed down a cation exchange resin (Dowex 50 H+ form) from which the inhibitors were un-retained. The extract was applied to a HP20 resin and three active fractions obtained; unbound, 25% methanol elution and 10% acetone in methanol elution.

All showed enzyme inhibition and similar chemical profiles but the 10% acetone in methanol fraction was more suitable for compound purification. Further chromatography of this fraction by polar flash chromatography on silica and preparatory and semi-preparatory HPLC on C18 gave seven compounds shown in FIG. 1. Five have been previously reported; quercitrin (1), rhamnitrin (3) and rhamnocitrin (4), quercitrin-3-O"-acetate (5) and parthenocissin A (6) and two were novel, 3-O-rhamnopyranosylkaempferol (2) and 3-(4-hydroxybenzylidene)-2-(2,5-dihydroxyphenyl)-1-(4-hydroxyphenyl)indane-4,6-diol (7).

Inhibition of Enzyme Activity

As shown in FIG. 2, all but one of the flavonoids show good α-amylase inhibition. Quercitrin (1) differs from the novel 3-O-rhamnopyranosylkaempferol (2) only by one hydroxyl substituent but this results in a decrease in α-amylase inhibition. However, methylation of a ring hydroxyl, in the case of rhamnitrin (3), or acetylation of the sugar, in the case of quercitrin-3-O"-acetate (5) causes the inhibition to be restored. All the flavonoids show similar response to lipase inhibition but again the inhibition of α-glucosidase shows variation for the various structural features.

The two indanes, 6 and 7 display significantly different inhibition profiles. Parthenocissin A (6) shows good inhibition of α-amylase whereas the novel 3-(4-hydroxybenzylidene)-2-(2,5-dihydroxyphenyl)-1-(4-hydroxyphenyl)indane-4,6-diol (7) is fairly specific as an inhibitor of the α-glucosidase.

Our experiments did not determine the $K_i$ values of the more potent of the individual inhibitors since we were more interested in indicating the combined effect of multiple inhibitors taken together as found for the original extract. It is important in such studies, however, to look for some specificity of inhibition to prove that the inhibition is not a therapeutically unattractive non-specific interaction with proteins in general. We have shown here that the compounds show specific inhibition of different enzymes. The inhibition of lipase did not go above 60% even with use of the commercial inhibitor Orlistat® at the same top concentration. The lipase and amylase seemed much more prone to inhibition by the *C. quadrangularis* components in general than the α-glucosidase.

The presence of several components exhibiting inhibition of amylase, lipase and glucosidase suggests that the plant could well have an effect on the ability of the gastrointestinal tract to utilize the plant and other sources of nutrients efficiently. Inhibitors of lipase such as Orlistat® and glucosidases such as Glyset® and Acarbose® are used as drugs to treat obesity and diabetes type 2. These drugs, however, often cause side-effects and it may well be that the combination of several tested components in *C. quadrangularis* working on different enzymes has a better tolerated effect and reduces or eliminates side effects associated with commercially available pharmaceuticals.

Although the combined effect of the aqueous extract was inhibition of the glucosidase activity, it is of interest to note that 1 and 5 actually promoted the glucosidase activity. Such promotion of enzyme activity can be due to binding to allosteric sites on the enzyme. While the effect of increased glucosidase activity by some components on weight control or diabetes is difficult to understand, there are many α-glucosidases present in the gastrointestinal tract and within cells and inhibition of some may be beneficial to the control of weight or diabetes whereas increased activity of certain glucosidases may be promoting health in other ways. We have only used one α-glucosidase here and the compounds may vary in effects and activity on other α-glucosidases. The ability of the individual components identified to reach the sites of enzyme activity will also vary and will be influenced by individual differences and no doubt also by variations in other food consumed with *C. quadrangularis* and formulation of products containing it.

The inhibition of α-glucosidases has been shown to be potentially therapeutically useful in diseases other than diabetes type 2 and weight control [6]. In particular such inhibitors have been studied as potential anti-viral and anti-cancer agents and it may well be that inhibition of α-glucosidases by *C. quadrangularis* explains the wide traditional medicinal use of the species. Promotion of specific glycosidase activities can also be therapeutic where those enzymes are deficient [6].

Experimental

Structure Elucidation

Structure elucidation was carried out using NMR (Bruker DRX500) for full $^1H$ and $^{13}C$ assignments and LCMS (Waters Integrity), which gave EIMS data for molecular weight and/or fragmentation assignment. All of the compounds would require further work (optical rotation measurements and/or x-ray crystallography) to ascertain stereochemistry.

Literature searches were conducted using the *Dictionary of Natural Products* (DNP) available on CDROM.

Plant Material

*Cissus quadrangularis* was supplied dry from the Cameroon. The reference for the voucher specimen for *Cissus quadrangularis* is No. 18668/SRF/Cam, identified by the Cameroon National Herbarium, Yaounde, Cameroon.

Extraction and Isolation

The dried *Cissus quadrangularis* (2.3 kg) was extracted in 50% aqueous ethanol (10 L) overnight. The filtered extract was loaded on two cation exchange columns (Dowex 50 H$^+$ form, 700 cm$^3$) from which the inhibitors were un-retained. The extract (8 L) was applied to a HP20 cartridge (6×75 cm) pre-equilibrated with 50% aqueous methanol (5 L) and eluted with 25% aqueous methanol (3 L) followed by 10% acetone in methanol (6 L) to give three active fractions; unbound (37 g), 25% methanol elution (27 g) and 10% acetone in methanol elution (14 g). All showed enzyme inhibition and similar chemical profiles but the 10% acetone in methanol fraction was more suitable for compound purification. The 10% acetone in methanol extract was bound onto silica and applied to a KP-Sil™ silica Flash 75S cartridge (7.5×9.0 cm) pre-equilibrated with heptane (5 L) and eluted with 75% heptane in ethyl acetate (1 L), 50% heptane in ethyl acetate (1 L), 25% heptane in ethyl acetate (1 L), 100% ethyl acetate (1 L) and 95% ethyl acetate in methanol (1 L) to give 5 fractions.

Preparatory HPLC of fraction 4 on Water's Nova-Pak® HR C18 column (2×(40×100 mm) in series, 6 μm, 60 A° at a flow rate of 55 ml/min and monitoring wavelength of 225 nm with an acetonitrile/water gradient; 80% water:20% acetonitrile containing 0.1% TFA to 65% water:35% acetonitrile containing 0.1% TFA over 15 mins, gave rise to parthenocissin A (6). Further purification of this fraction on Water's Nova-Pak® HR C18 column (25×100 mm, 6 µm, 60 A° at a flow rate of 15 ml/min and monitoring wavelength of 225 nm with an methanol/water gradient; 55% water:45% methanol containing 0.1% TFA to 30% water:70% methanol containing 0.1% TFA over 15 mins, gave rise to quercitrin-3-O"-acetate (5) and 3-(4-hydroxybenzylidene)-2-(2,5-dihydroxyphenyl)-1-(4-hydroxyphenyl)indane-4,6-diol (7). Preparatory HPLC of fraction 5 on Water's Nova-Pak® HR C18 column (2×(40×100 mm) in series, 6 µm, 60 A° at a flow rate of 55 ml/min and monitoring wavelength of 210 nm with an acetonitrile/water gradient, 80% water:20% acetonitrile containing 0.1% TFA to 60% water:40% acetonitrile containing 0.1% TFA over 20 mins, gave rise to quercitrin (1), 3-O-rhamnospyranosylkaempferol (2), rhamnitrin (3) and rhamnocitrin (4).

Kits and Reagents Used for Bioassays

The purified compounds and extracts were made up 2 mg/ml solutions in water using initially a drop of DMSO if required for solubility.

Lipase

Sigma Lipase-PS Kit (Catalogue Number 805-A)

Human pancreatic lipase was diluted 1.5:5 prior to use. The assay was carried out at 20° C. using 10 µl test compound, 5 µl enzyme solution, 90 µl substrate, and 30 µl activator reagent. Color formation was measured at 550 nm after 30 minutes.

Amylase

Sigma INFINITY Powder Reagent (Catalogue Number 568-20)

Sigma α-amylase (A6255, porcine pancreatic amylase as saline suspension), diluted to 35 units/ml. The assay was carried out at 20° C. using 10 µl enzyme solution, 10 µl test compound, and 150 µl INFINITY reagent. The rate of color formation was measured over five minutes, after which the final absorbance was measured at 405 nm as an endpoint recording.

α-Glucosidase

Sigma α-glucosidase (G5003, from *S. cerevisiae*) at 2 units/ml in phosphate buffer pH 6.0. Sigma p-nitrophenyl-α-D-glucopyranoside, 5 mM in phosphate buffer pH 6.0. The assay was carried out at 20° C. using 10 µl enzyme solution, 10 µl test compound, and 50 µl substrate solution. The reaction was carried out for 7 minutes; color formation was measured at 415 nm following the addition of 80 µl 0.4 M glycine solution, pH 10.4 to stop the reaction. Other glycosidase assays were carried out using enzymes from Sigma and appropriate p-nitrophenyl substrates [7].

3-O-rhamnopyranosylkaempferol (2)

UV/Vis $\lambda_{max}$ (MeOH) nm (log ε): 200, 264, 342 $^1$H NMR (500 MHz, MeOH) δ ppm 0.79 (3H, d, J=6 Hz), 3.23 (1 H, m), 3.59 (1 H, m), 3.59 (1 H, m), 4.11 (1 H, m), 5.27 (1H, d, J=2 Hz), 6.10 (1H, d, J=2 Hz), 6.27 (1H, d, J=2 Hz), 6.84 (2H, dd, J=2.9 Hz), 7.67 (2H, dd, J=2.9 Hz). $^{13}$C NMR (500 MHz, MeOH) δ ppm 18.0 (CH$_3$), 72.3 (CH), 72.4 (CH), 72.6 (CH), 73.6 (CH), 95.2 (CH), 100.3 (CH), 103.9 (CH), 106.4 (C), 117.0 (2×CH), 123.1 (C), 132.3 (2×CH), 136.7 (C), 159.0 (C), 159.7 (C), 162.0 (C), 163.7 (C), 166.3 (C), 180.1 (C=O). HPLC-MS: m/z, 288 (100) (C$_{21}$H$_{22}$O$_{10}$), 257, 120.

3-(4-hydroxybenzylidene)-2-(2,5-dihydroxy-phenyl)-1-(4-hydroxyphenyl)indane-4,6-diol (7)

UV/Vis $\lambda_{max}$ (MeOH) nm (log ε): 200, 323 $^1$H NMR (500 MHz, MeOH) δ ppm 4.21 (1H, broad s), 4.36 (1H, broad s), 6.27 (1H, t, J=2 Hz), 6.35 (1H, d, J=2 Hz), 6.41 (2H, d, J=2 Hz), 6.81 (4H, dd, J=2.9 Hz), 6.88 (1 H, d, J=2 Hz), 7.07 (2H, dd, J=2.9 Hz), 7.16 (1H, s), 7.29 (2H, d, J=9 Hz). $^{13}$C NMR (500 MHz, MeOH) δ ppm 58.5 (CH), 61.6 (CH), 98.9 (CH), 102.0 (CH), 104.3 (CH), 107.1 (2×CH), 116.3 (2×CH), 116.4 (2×CH), 123.6 (CH), 125.9 (C), 129.3 (2×CH), 129.6 (2×CH), 130.7 (C), 131.6 (CH), 139.0 (C), 143.8 (C), 148.0 (C), 148.1 (C), 150.1 (C), 156.5 (C), 156.9 (C), 157.8 (C), 160.1 (2×C). HPLC-MS: M$^{\cdot+}$ 454 (C$_{28}$H$_{22}$O$_6$, m/z 360, 347 (100), 331, 239, 227, 226, 215, 199, 180, 149, 107, 95.

REFERENCES

[1] Chopra S, Patel M, Gupta L and Datta I. (1975) Studies on *C. quadrangularis* in experimental fracture repair: Effect on chemical parameters in blood. *Indian Journal of Medicinal Research*, 63: 824-828.

[2] Oben J, Kuate D, Agbor G, Momo C and Talla X. (2006) The use of a *C. quadrangularis* formulation in the management of weight loss and metabolic syndrome. *Lipids in Health and Disease*, 5; 24-30.

[3] Agbor G, Kuate D, Oben J. (2007) Medicinal plants can be a good source of antioxidant: Case study of Cameroon, *Pakistan Journal of Biological Science*, 10, 537-544.

[4] Mallika J and Shyamala C. (2005) In vitro and in vivo evaluation of free radical scavenging potential of *C. quadrangularis*. *African Journal of Biomedical Research.*, 8: 95-99.

[5] Mehta M, Kaur N, Bhutani K K. (2007) Determination of marker constituents from *Cissus quadrangularis* Linn. and their quantization by HPTLC and HPLC. *Phytochemical Analysis* 12, 91-105.

[6] Watson A, Fleet G W J, Asano N, Molyneux R J and Nash R J (2001) Polyhydroxylated Alkaloids—Natural Occurrence and Therapeutic Applications. *Phytochemistry* 56, 265-295.

[7] Watson A, Nash R, Wormald M, Harvey D, Dealler S, Lees E, Asano N, Kizu H, Kato A, Griffiths R C, Cairns A J and Fleet G W J. (1997) Glycosidase-inhibiting pyrrolidine alkaloids from *Hyacinthoides non-scripta*. *Phytochemistry* 46, 255-259.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

What is claimed is:

1. A method for reducing body weight in a mammal comprising:
   a. providing a composition containing an effective amount of purified and isolated 3-(4-hydroxybenzylidene)-2-(2, 5-dihydroxyohenyI)-1-(4-hydroxyphenyl)indane-4,6-diol;
   b. administering the composition to a mammal in need thereof;
   wherein the effective amount of the composition is 10 mg to 900 mg daily.

2. A method of claim 1, wherein the effective amount of the composition provided to the mammal is 50 mg to 200 mg daily.

* * * * *